United States Patent
Sharkey

(10) Patent No.: US 9,572,672 B2
(45) Date of Patent: Feb. 21, 2017

(54) METHODS AND DEVICES FOR PATELLAR RESURFACING TREATMENT

(71) Applicant: ZIMMER KNEE CREATIONS, INC., Exton, PA (US)

(72) Inventor: Peter F. Sharkey, Villanova, PA (US)

(73) Assignee: ZIMMER KNEE CREATIONS, INC., Exton, PA (US)

(*) Notice: Subject to any disclaimer, the term of this patent is extended or adjusted under 35 U.S.C. 154(b) by 0 days.

(21) Appl. No.: 14/794,950

(22) Filed: Jul. 9, 2015

(65) Prior Publication Data

US 2015/0305875 A1 Oct. 29, 2015

Related U.S. Application Data

(63) Continuation-in-part of application No. PCT/US2014/025452, filed on Mar. 13, 2014.

(60) Provisional application No. 61/784,609, filed on Mar. 14, 2013.

(51) Int. Cl.
*A61F 2/38* (2006.01)
*A61F 2/30* (2006.01)

(52) U.S. Cl.
CPC .......... *A61F 2/3877* (2013.01); *A61F 2/30771* (2013.01); *A61F 2002/302* (2013.01); *A61F 2002/30115* (2013.01); *A61F 2002/30878* (2013.01); *A61F 2002/30892* (2013.01)

(58) Field of Classification Search
CPC ............ A61F 2/3877; A61F 2002/3881; A61F 2/30771; A61F 2/38; A61F 2/3872; A61F 2002/30115; A61F 2002/302; A61F 2002/30878

USPC ............................................ 623/20.17, 20.18
See application file for complete search history.

(56) References Cited

U.S. PATENT DOCUMENTS

| 4,944,756 A * | 7/1990 | Kenna .................. A61B 17/155 623/20.19 |
| 4,954,867 A | 9/1990 | Hosaka |
| 4,964,867 A | 10/1990 | Boger |
| 5,236,462 A * | 8/1993 | Mikhail .............. A61F 2/30767 623/20.2 |
| 5,522,901 A * | 6/1996 | Thomas ................ A61F 2/3877 623/20.2 |
| 6,146,423 A * | 11/2000 | Cohen ................. A61F 2/3877 623/20.2 |

(Continued)

FOREIGN PATENT DOCUMENTS

| EP | 0812581 A2 | 12/1997 |
| WO | WO-2012078653 A1 | 6/2012 |
| WO | WO-2014159919 A1 | 10/2014 |

OTHER PUBLICATIONS

"International Application Serial No. PCT/US2014/025452, International Search Report mailed Jul. 21, 2014", 4 pgs.

(Continued)

*Primary Examiner* — Alvin Stewart
(74) *Attorney, Agent, or Firm* — Schwegman Lundberg & Woessner, P.A.

(57) ABSTRACT

Certain disclosed examples provide methods for strengthening, reinforcing, and/or stimulating repair of residual patella bone to be resurfaced. Also provided in some examples are devices associated with the methods. These methods and devices may be utilized during or following total knee replacement (TKR) or total knee arthroscopy (TKA).

19 Claims, 7 Drawing Sheets

(56) References Cited

U.S. PATENT DOCUMENTS

| | | | |
|---|---|---|---|
| 6,855,150 B1* | 2/2005 | Linehan | A61B 17/1767 606/96 |
| 2003/0088315 A1* | 5/2003 | Supinski | A61F 2/3877 623/20.2 |
| 2004/0236428 A1* | 11/2004 | Burkinshaw | A61F 2/3877 623/20.15 |
| 2004/0254645 A1* | 12/2004 | Arnin | A61F 2/3877 623/20.2 |
| 2007/0265708 A1* | 11/2007 | Brown | A61F 2/3877 623/20.2 |
| 2008/0177394 A1 | 7/2008 | Chauhan | |
| 2012/0101584 A1* | 4/2012 | Amirouche | A61B 17/1767 623/20.2 |
| 2013/0166035 A1* | 6/2013 | Landon | A61F 2/3877 623/20.2 |
| 2014/0277523 A1* | 9/2014 | Masini | A61F 2/3877 623/20.2 |

OTHER PUBLICATIONS

"International Application Serial No. PCT/US2014/025452, Written Opinion mailed Jul. 21, 2014", 6 pgs.
"European Application Serial No. 14729495.3, Response filed May 16, 2016 to Communication pursuant to Rules 161(1) and 162 EPC mailed Nov. 5, 2015", 10 pgs.
"International Application Serial No. PCT/US2014/025452, International Preliminary Report on Patentability mailed Sep. 24, 2015", 8 pgs.

* cited by examiner

METHODS AND DEVICES FOR PATELLAR RESURFACING TREATMENT

RELATED APPLICATIONS

This patent application is a continuation-in-part, and claims the benefit of priority of, International Application No. PCT/US2014/025452, filed on Mar. 13, 2014 at the United States Receiving Office, which claims the benefit of U.S. Provisional Patent Application Ser. No. 61/784,609, filed on Mar. 14, 2013, the entire of each of the disclosures of the afore-mentioned patent documents is explicitly incorporated by reference herein.

TECHNICAL FIELD

This patent document pertains generally, but not by way of limitation, to methods for patellar repair and associated devices for such methods. More particularly, the present method and devices can strengthen and/or stimulate repair of residual patella bone during patellar resurfacing.

BACKGROUND

During many total knee replacement (TKR) or total knee arthroscopy (TKA) procedures, the patella is frequently resurfaced, such as with a polymer like polyethylene. Despite this resurfacing, a moderate number of post-TKA patients still experience anterior knee pain and their technetium bone scans can show an increased activity in the patella. This increased activity is believed to be due to overstressed bone.

Some theories exist to explain why the patella is often overstressed following TKA. Since patellar resurfacing components are typically formed from polymer-based materials, like polyethylene, this increases stress transfer to the bone. Patellar resurfacing components tend not to have a metal backing since the inclusion of the metal backing creates other wear problems. Another theory proposed is that the TKA components do not perfectly duplicate normal knee kinematics and this also increases forces on the knee extensor mechanism and the patella. Still another theory is that, if during resurfacing, the patella is resected too thick, too thin, or asymmetrically, this would result in increased strain in the patella bone.

Accordingly, there exists a need for treatments and devices that would strengthen and/or stimulate repair of residual patella bone following TKA, or if the surgeon deems necessary, in conjunction with the TKA procedure. These patellar treatments and devices would ideally avoid the setbacks described above with current treatments and devices, including the high incidence of patellar complications following TKA or TKR procedures.

SUMMARY

In general, the present disclosure provides methods and devices for strengthening, reinforcing, and/or stimulating repair of residual patella bone following total knee replacement (TKR) or total knee arthroscopy (TKA). The methods and devices may also be performed, if the surgeon deems necessary, in conjunction or at the same with the TKR or TKA procedure.

Accordingly, in one example, a patellar resurfacing system is provided. This particular system comprises a patellar resurfacing implant that includes a bone-contacting surface for placement against a resected patella bone. The patellar resurfacing implant also includes a first extension that extends from the bone-contacting surface for placement in a corresponding void formed in the resected patella bone. The system also includes a first load-sharing ring implantable in the resected patella bone for contacting the bone-contacting surface of the patellar resurfacing implant.

Another example provides a method of resurfacing a patella bone. This particular method includes a step of providing a patellar resurfacing implant that includes a bone-contacting surface for placement against a resected patella bone where the patellar resurfacing implant includes a first extension that extends from the bone-contacting surface for placement in a corresponding void formed in the resected patella bone. In another step, a patella bone is resected to form a resected patella bone. In another step, a void is formed in the resected patella bone. In another step, a first load-sharing ring is implanted in the resected patella bone. In another step, the patellar resurfacing implant is implanted which includes placing the bone-contacting surface of the patellar resurfacing implant against the resected patella bone and placing the first extension in the void formed in the resected patella bone. Implanting the patellar resurfacing implant in the resected patella bone can bring the bone-contacting surface into contact with the first load-sharing ring, e.g., around the full circumference of the first load-sharing ring.

Still another example provides an implantable device for mechanically strengthening a resected patella bone prior to receiving a patellar resurfacing component. The device may comprise a metallic ring configured for placement within the resected patella bone. The ring may further include a biologically active coating to stimulate bone healing. This biologically active coating can induce tissue ingrowth. In some cases, the metallic ring can comprise Nitinol or other shape memory metal or alloy. In addition, the metallic ring may comprise a sharp cutting edge for insertion into the patella.

In another example, a method of mechanically strengthening resected patella bone for resurfacing is provided. The method may comprise resecting the patella bone, drilling one or more holes in the patella bone to receive a patellar resurfacing component, inserting a metallic ring into the patella bone, injecting a bonding material into the one or more holes, and placing the patellar resurfacing component onto the resected patella bone. The patellar resurfacing component may comprise a polymeric material, while the bonding material may comprise a methacrylate such as for example polymethylmethacrylate. In addition, the metallic ring can comprise Nitinol or other shape memory metal or alloy. The method may further comprise heating the metallic ring prior to inserting into the patella bone. In addition, the metallic ring can further comprise a biologically active coating. In some embodiments, more than one metallic ring is inserted into the patella bone.

In still another example, a system for mechanically strengthening resected patella bone prior to receiving a patellar resurfacing component is provided. The system may comprise a set of metallic rings configured for placement within the resected patella bone. The set of metallic rings may comprise concentric rings. One of the metallic rings can comprise Nitinol or other shape memory metal or alloy. In addition, the metallic rings may comprise a sharp cutting edge for insertion into the patella. Each of the rings may further include a biologically active coating to stimulate bone healing.

To better illustrate the patellar resurfacing systems and method disclosed herein, a non-limiting list of examples is provided here:

Example 1 can include subject matter (such as a system) comprising a load-sharing implant having a superior surface, an inferior surface, and at least one hole extending from the superior surface to the inferior surface, the load-sharing implant configured to be received within a corresponding recess formed in a resected patella bone, and a patellar resurfacing implant having an engaging surface for placement against the resected patella bone and the superior surface of the implant, the patellar resurfacing implant including at least one projection extending from the engaging surface, wherein the at least one projection is configured to extend through the load-sharing implant hole and into a corresponding void formed in the recess.

In Example 2, the subject matter of Example 1 can optionally include where a diameter of the patellar resurfacing implant is greater than a diameter of the load-sharing implant.

In Example 3, the subject matter of Example 1 can optionally include where the load-sharing implant is coated with a biologically active coating for stimulating bone healing in the resected patella bone.

In Example 4, the subject matter of Example 1 can optionally include where the load-sharing implant includes Nitinol.

In Example 5, the subject matter of Example 1 can optionally include where the load-sharing implant includes a plurality of holes and the patellar resurfacing implant includes a plurality of projections.

In Example 6, the subject matter of Example 5 can optionally include where a number of holes in the load-sharing implant is at least one of: equal to or greater than a number of projections of the patellar resurfacing implant.

In Example 7, the subject matter of Example 5 can optionally include where each projection of the plurality of projections is configured to be received within a corresponding hole of the load-sharing implant.

In Example 8, the subject matter of Example 5 can optionally include where each hole of the plurality of holes is equidistant from the other holes.

In Example 9, the subject matter of Example 1 can optionally include where the hole is a first hole and the load-sharing implant includes a second hole and a third hole, and wherein the projection is a first projection and the patellar resurfacing implant includes a second projection and a third projection.

Example 10 can include subject matter (such as a method) comprising resecting a patella bone to form a resected patella bone having a resected patella surface, forming a recess in the resected patella bone, the recess having a recessed patella surface, forming a void in the recessed patella surface, implanting a load-sharing implant into the recess, the load-sharing implant having a superior surface, an inferior surface, and a hole extending from the superior surface to the inferior surface, wherein the hole is aligned with the void, and implanting a patellar resurfacing implant into the resected patella bone, the patellar resurfacing implant including an engaging surface and a projection extending from the engaging surface.

In Example 11, the subject matter of Example 10 can optionally include implanting the patellar resurfacing implant in the resected patella bone includes inserting the projection through the hole of the load-sharing implant and into the corresponding void formed in the recessed patella surface.

In Example 12, the subject matter of Example 11 can optionally include placing the engaging surface of the patellar resurfacing implant against the resected patella surface.

In Example 13, the subject matter of Example 11 can optionally include where, prior to placing the first extension in the void, injecting a bonding material into at least one of: the void formed in the recessed patella surface and the hole in the load-sharing implant.

In Example 14, the subject matter of Example 13 can optionally include where the bonding material includes a methacrylate.

In Example 15, the subject matter of Example 10 can optionally include where implanting the patellar resurfacing implant in the resected patella bone brings the engaging surface into contact with the superior surface of the load-sharing implant.

In Example 16, the subject matter of Example 10 can optionally include where inserting the load-sharing implant into the recess includes press fitting the load-sharing implant into the recess.

In Example 17, the subject matter of Example 10 can optionally include where, when the load-sharing implant is inserted in the recess, the superior surface of the implant is substantially flush with the resected patella surface.

In Example 18, the subject matter of Example 10 can optionally include where the implant includes a metallic material.

In Example 19, the subject matter of Example 10 can optionally include where the load-sharing implant includes two or more holes and the patellar resurfacing implant includes a number of projections that is equal to or less than a number of holes in the load-sharing implant.

Example 20 can include subject matter (such as a system) comprising a metallic implant having a superior surface, an inferior surface, an edge connecting the superior surface to the inferior surface, and three holes extending through the superior surface to the inferior surface, the load-sharing implant configured to be received within a corresponding recess formed in a resected patella bone, and a patellar resurfacing implant having an engaging surface for placement against the resected patella bone and the superior surface of the load-sharing implant, the patellar resurfacing implant including three projections extending from the engaging surface, wherein each projection is configured to extend through a corresponding hole and into a corresponding void formed in the recess.

Example 21 can include, or can optionally be combined with any portion or combination or any portions of any one or more of Examples 1-20 to include, subject matter that can include means for performing any one or more of the functions of Examples 1-20.

These non-limiting examples can be combined in any permutation or combination.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several examples of the disclosure and together with the description, serve to explain the principles of the disclosure.

DESCRIPTION OF THE EMBODIMENTS

Methods and devices for strengthening and/or stimulating repair of residual patella bone during or following total knee replacement (TKR) or total knee arthroscopy (TKA) are provided. In general, the disclosure provides methods and devices relating to the resurfacing treatment of the patella, which may be performed at the same time as, or following, other knee treatments as mentioned above.

Figure 1:
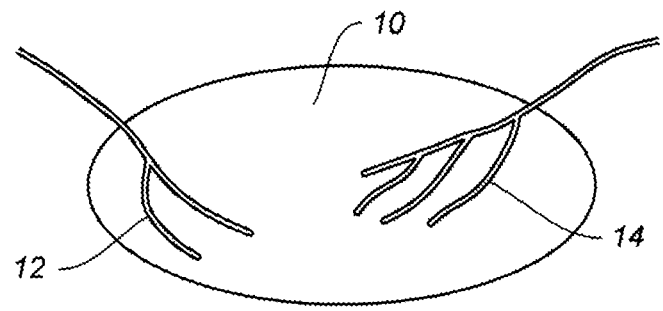
FIG. 1 represents a perspective view of a native patella and associated blood supply to the patella.

Patellar complications after total knee replacement (TKR) or total knee arthroscopy (TKA) are common and include anterior knee pain, component loosening and bone fracture. During TKR/TKA, patellar resurfacing is associated with substantial effects on the physiology and mechanical properties of this bone. For instance, exposure of the knee joint requires arthrotomy of the joint capsule which disrupts a large portion of the blood supply to the patella 10, including the lateral blood supply 12 and medial blood supply 14, as represented in FIG. 1. If a lateral retinacular release is required to achieve proper patella tracking, near complete or even complete patella blood supply is compromised.

Figure 2:
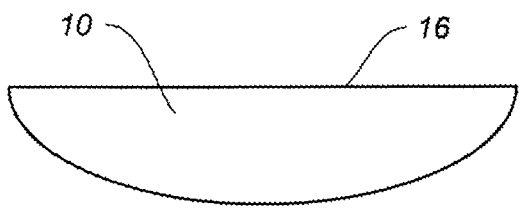
FIG. 2 illustrates a cross-sectional view of a resected patella.

In order to resurface the patella 10, the articular surface of the bone is resected, as shown in FIG. 2, to create a flat surface 16 for applying a patellar resurfacing component 20. As previously disclosed, current patellar resurfacing components 20 are formed of polymeric materials like polyethylene and the like. Approximately 9 mm of bone is generally removed (same thickness as replacement part). The natural patella 10 varies in thickness, with an average thickness of 21 mm in women and 25 mm in men. Therefore, resection of 9 mm of native bone weakens the residual bone and increases tensile stresses in the diminished residual bone volume.

Figure 3:
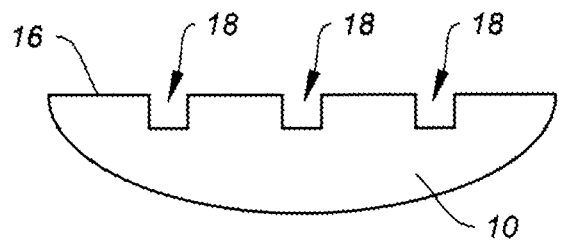
FIG. 3 illustrates a cross-sectional view of the patella with holes drilled in for receiving a patellar resurfacing component.

After resection, one or more voids or holes 18 are generally drilled in the resected patella 10 to accommodate the fixation pegs of the patellar replacement component 20. As shown in FIG. 3, three holes 18 may be drilled into the resected patellar surface 16 in order to accommodate the anchorage of the patellar replacement component 20. Drilling these holes 18, which are necessary for the attachment of the patellar replacement component 20, further weakens the bone and creates stress risers.

Figure 4:
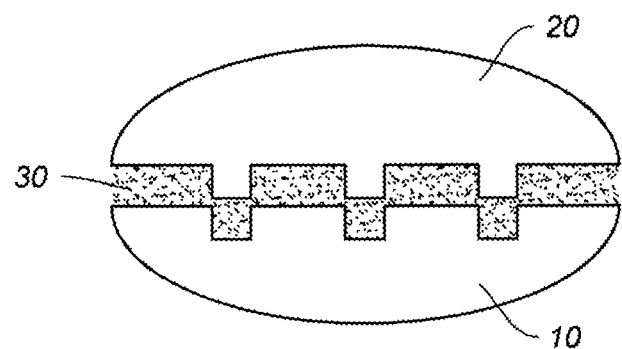
FIG. 4 illustrates an exploded view of a patellar resurfacing system.

As shown in FIG. 4, the patellar resurfacing component 20 can be fixed to the resurfaced surface 16 of the patella 10 with an injectable bonding material 30 such as, for example, a methacrylate like polymethylmethacrylate (PMMA) 30. Methacrylates such as polymethylmethacrylate is a very common bonding material used in current patellar resurfacing techniques today. The PMMA 30 may be injected in the three fixation holes 18 using, for instance, a pressurized cement gun or other known injection instrument. The intrusion of PMMA replaces normal cancellous bone and results in the creation of non-biologic regions. These non-biologic regions are incapable of biologic bone remodeling, such bone remodeling representing an appropriate response to redistribution of forces in the new construct.

Figure 5:
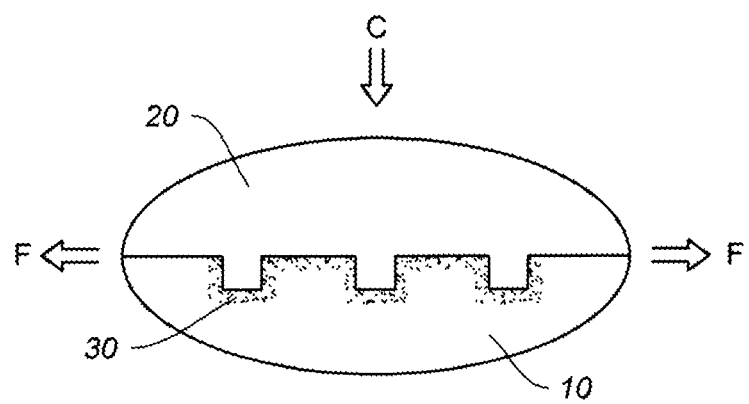
FIG. 5 illustrates a cross-sectional view of the resurfaced patella of FIG. 4.

It is believed that the native and resurfaced patella 10 is subjected to large compressive and tensile forces on the order of magnitude of several multiples greater than the patient's body weight. The tensile forces F are created by the attachment of the quadriceps tendon to the proximal pole of the patella 10 and the patellar tendon attachment to the distal pole. Additionally, tissue called the knee retinaculum is attached medially and laterally to the patella 10 and high tensile forces are created at these interfaces, as represented in FIG. 5.

In general, PMMA resists compressive forces C very effectively, but demonstrates low strength when tensile forces F are applied to the material. These characteristics of PMMA, combined with biologic inhibition of bone remodeling and compromised mechanical properties of the residual patella bone 10, likely is responsible for the unacceptably high incidence of patella complications following TKR or TKA procedures. Perhaps the most revealing evidence is that clinical studies have failed to demonstrate a significant improvement in clinical results when comparing the TKR or TKA performed with or without patellar resurfacing.

Thus, the results of TKR or TKA, specifically less anterior knee pain and fewer patellar complications, could be improved with biologic and/or mechanical enhancement of the residual, resurfaced patella bone 10. The present examples accomplish these goals. In one embodiment, a method comprises a patella preparation for resurfacing and patellar resurfacing component fixation methods using a bonding material such as PMMA. However, after bone preparation, but prior to resurfacing component fixation with PMMA, an implantable device 40 with biologic and mechanical enhancing properties may be inserted into the patella bone 10. This implantable device 40, which may comprise a 3-dimensional metal insert with biologic coating, would incorporate into the native residual bone. Once incorporated, the device 40 would serve as a load sharing device with the aforementioned forces F, C dampened by the device 40.

Figure 6:
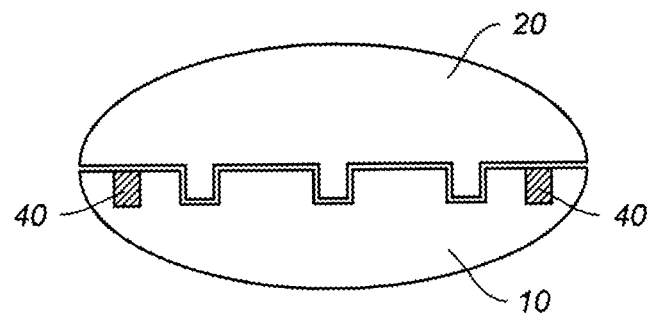
FIG. 6 illustrates a cross-sectional view of the resurfaced patella of FIG. 4 with an exemplary implantable device of the present disclosure.
Figure 7:
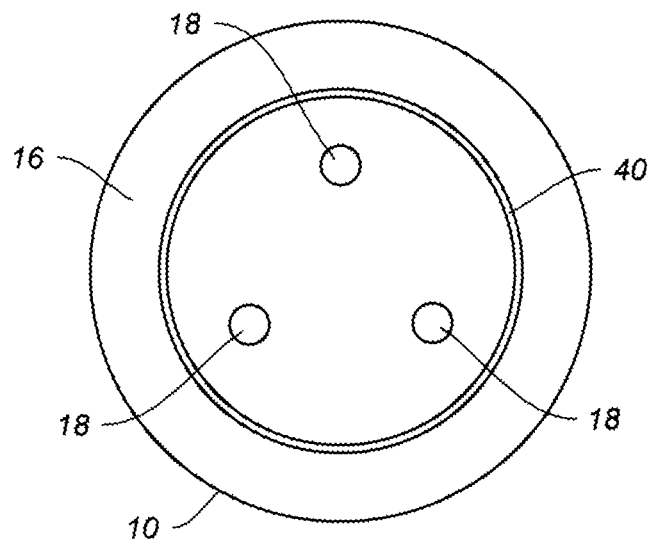
FIG. 7 illustrates a top-down view of the resected patella with implantable device of FIG. 6.

With this device 40 accepting a portion of the forces F, C on the patella 10, the residual bone would be subjected to lower stresses. In one embodiment, the implantable device 40 can be approximately 3 mm thick and extend about 5 mm into the bone 10. The implantable device 40 may be constructed as a 3-dimensional metal insert and possibly be biologically coated. For example, as shown in FIGS. 6 and 7, the implantable device 40 may take the form of a ring. This ring may be configured for easy insertion onto the resected surface 16 of the patella 10 with little force required. In one example, the ring may have a sharp or serrated edge for cutting into bone tissue such that the surgeon can apply downward force onto the ring to insert it into the patella 10. In another example, the ring may be simply tapped or hammered into place, without requiring such force as to damage the residual patella 10.

Figure 8:
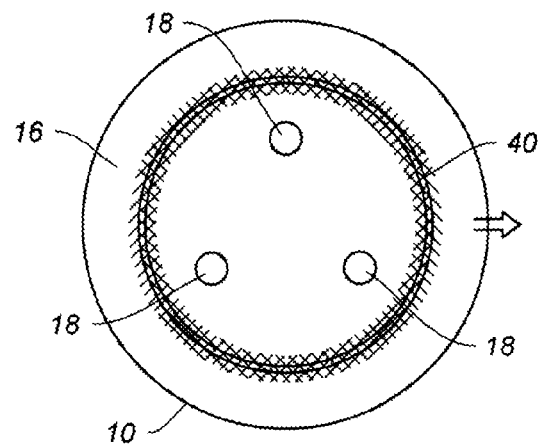
FIG. 8 illustrates a top-down view of the patella with implantable device of FIG. 7 over time.

In one embodiment, as shown in FIG. 7, the implantable device 40 may be inserted so that the ring encircles or otherwise extends around the drilled holes 18 on the resected surface 16. Once ingrowth into the device 40 is achieved, it would become a load sharing device and reduce forces delivered to the residual patella bone 10, as represented in FIG. 8. If coated with an agent stimulating angiogenesis, the device 40 may also improve blood supply to the bone over time.

In another exemplary embodiment, the implantable device 40 may comprise a Nitinol or other shape memory metal or alloy ring that may be heated to expand and then inserted into the patella 10. After cooling off inside the patella 10, the ring would contract and provide a continuous force within the patella 10. In other words, the Nitinol ring may serve to keep continuous tension within the patella 10 and function as a load sharing device.

Figure 9:
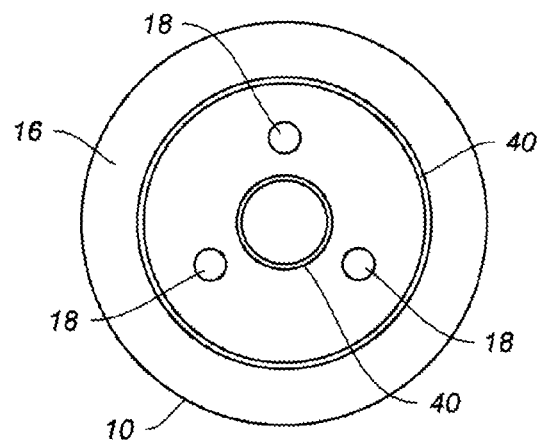
FIG. 9 illustrates a top-down view of another example of a resected patella with implantable devices of the present disclosure.
Figure 10:
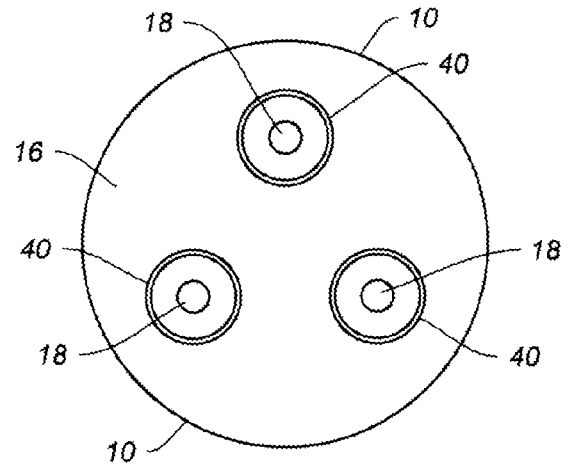
FIG. 10 illustrates a top-down view of still another example of a resected patella with implantable devices of the present disclosure.

Although illustrated in FIGS. 6-8 as a ring surrounding the drilled holes 18 of the resected surface 16, it is contemplated that the implantable device 40 may also be configured with a smaller overall dimension to be inserted so as to reside interior to the drilled holes 18. In addition, it is also understood that more than one implantable device 40 may be utilized in the methods of the present disclosure. For instance, as shown in FIG. 9, two or more rings may be utilized to achieve the same result of strengthening and improving patellar repair by sharing loads. In one example, the implantable devices can comprise two or more concentric rings, each ring comprising a metallic or Nitinol insert and having similar features to those already described. These rings can be placed around and within the drilled holes 18 to provide even greater load sharing capabilities. In another example, as shown in FIG. 10, the implantable devices 40 may comprise a set of metallic or Nitinol rings, each ring being configured for insertion around a drilled hole 18, such that each drilled hole 18 has a corresponding metallic ring surrounding it.

Figure 11:
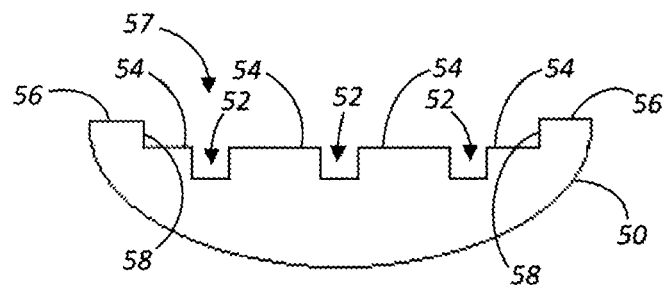
FIG. 11 illustrates a cross-sectional view of an example of a resected patella bone.

FIG. 11 illustrates a cross-sectional view of an example of a resected patella bone 50. Initially, the patella can be resected similarly to the patella 10 (as shown in FIG. 2) to create a flat surface, for example, resected patella surface 56. Subsequently or simultaneously, a recess 57 can be formed in the resected patella surface 56. The recess 57 can be defined by a recessed patella surface 54 and a shoulder 58.

Figure 16:
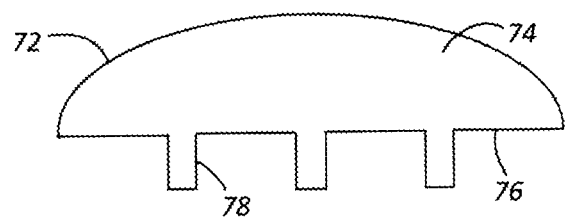
FIG. 16 illustrates a side view of an example of a patellar resurfacing implant.

After resection and forming the recess, one or more voids 52 can be formed in the recessed patella surface 54. The one or more voids 54 can be formed by drilling into the recessed patella surface 54. As discussed herein, the voids 54 can accommodate projections 78 (e.g., fixation pegs) of a patellar replacement component 72 (as shown in FIG. 16). As shown in FIG. 11, three voids 52 are drilled into the recessed patella surface 54 to accommodate the projections of the patellar replacement component 72. Generally, the number of voids 52 equals the number of projections since as the number of voids 52 decreases the strength of the bone and can create stress risers.

Figure 12:
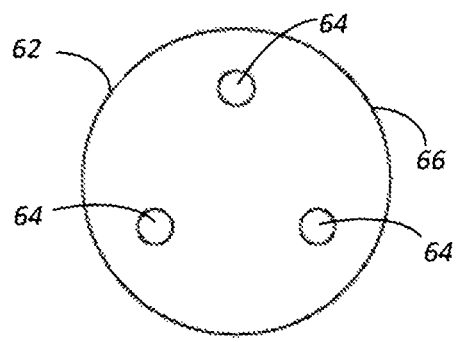
FIG. 12 illustrates a top-down view of an example of a load-sharing implant.
Figure 13:
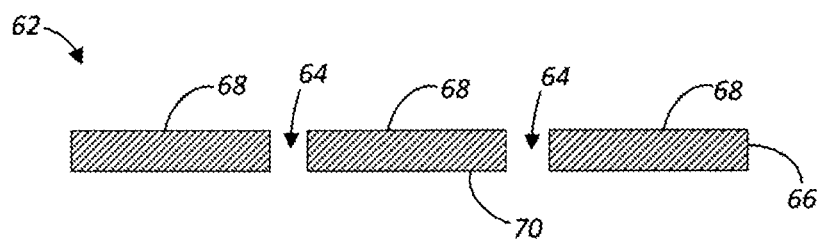
FIG. 13 illustrates a cross-sectional view of an example of the load-sharing implant.

FIGS. 12 and 13 illustrate examples of load-sharing implants 62. For example, FIG. 12 illustrates a top-down view of an example of a load-sharing implant 62 and FIG. 13 illustrates a cross-sectional view through two holes of an example of a load-sharing implant 62. As shown in FIG. 12, the load-sharing implant 12 includes three holes 64. As discussed herein, the number of holes 64 can correspond to the number of projections on the patellar resurfacing implant. To minimize any weakening caused by forming voids in the patella, the holes 64 of the load-sharing implant 62, which correspond to the voids in the patella, can be equidistant from each other. The load-sharing implant 12 includes a superior surface 68 and an inferior surface 70 with an edge 66 extending from the superior surface 68 to the inferior surface 70.

Figure 15:
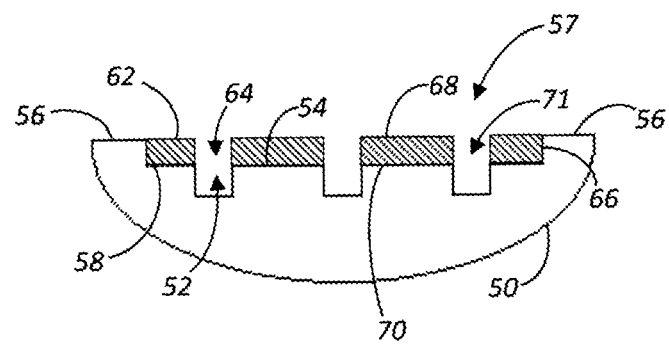
FIG. 15 illustrates a cross-sectional view of an example of the resected patella bone including the load-sharing implant.

The load-sharing implant 62 can be constructed as a 3-dimensional metal disc insert. In an example, the load-sharing implant 62 can be biologically coated. For example, as shown in FIGS. 12 and 13, the load-sharing implant 62 can take the form as a circular disc. However, other shapes can be sued. The shape of the load-sharing implant 62 can be configured for easy insertion into the recess 57 of the recessed patella bone 50 (as shown in FIG. 15). In an example, the load-sharing implant 62 can be press-fit into the recess. The load-sharing implant 62 can also have a sharp or serrated edge for cutting into bone tissue to further secure the load-sharing implant 62. While the load-sharing implant 62 in FIG. 12 includes three holes 64 and is circular, the shape of the load-sharing implant 62 and the shape, number, and spacing of the holes 62 can vary depending on the particular patient.

Figure 14:
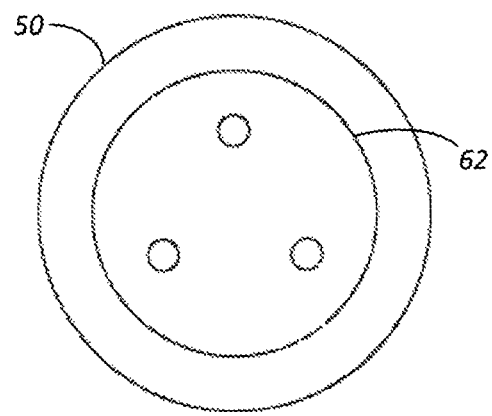
FIG. 14 illustrates a top-down view of an example of the resected patella bone including the load-sharing implant.

FIGS. 14 and 15 illustrate examples of the resected patella bone 50 including the load-sharing implant 62. For example, FIG. 14 illustrates a top-down view of an example of the resected patella bone 50 including the load-sharing implant 62 and FIG. 15 illustrates a cross-sectional view of an example of the resected patella bone 50 including the load-sharing implant 62. As shown in FIGS. 14 and 15, the load-sharing implant 62 can be implanted into the recess 57 of the resected patella bone 50. As discussed herein, the load-sharing implant 62 can be press-fit into the recess 57. Other coupling means can also be used.

The load-sharing implant 62 can be implanted into the recess 57 such that the holes 64 of the load-sharing implant 62 align with the voids 52 in the recessed patella bone 50 to form openings 71. As discussed herein, the openings 71 can be configured to receive a projection from the patellar resurfacing implant. When the load-sharing implant 62 is implanted, the inferior surface 70 can contact the recessed patella surface 54 and the edge 66 of the load-sharing implant 62 can be in contact with the shoulder 58 of the recess 57. In an example, the superior surface 68 can be substantially flush with or below the resected patella surface 56. In another example, the superior surface 68 can extend beyond the resected patella surface 56.

FIG. 16 illustrates a side view of an example of a patellar resurfacing implant 72. The patellar resurfacing implant 72 can include a body portion 74, an engaging surface 76, and one or more projections 78 extending from the engaging surface 76. As discussed herein, the number of projections 78 can equal the number the holes in the load-sharing implant. As discussed herein, the patellar resurfacing implant 72 can be formed of polymeric materials such as polyethylene.

Figure 17:
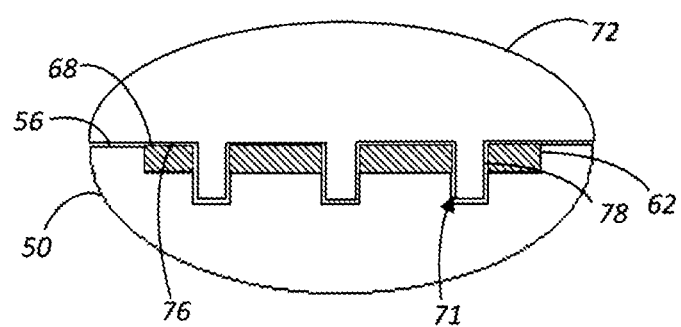
FIG. 17 illustrates a cross-sectional view of the resurfaced patella bone including the patellar resurfacing implant and the load-sharing implant.

FIG. 17 illustrates a cross-sectional view of the resurfaced patella bone 50 including the patellar resurfacing implant 72 and the load-sharing implant 62. The patellar resurfacing implant 72 can be implanted (e.g., or fixed) to the resected patella bone 50, for example, by using an injectable bonding material such as, for example, a methacrylate like PMMA. For example, after the load-sharing implant 62 is implanted into the recess of the resected patella bone, the bonding material can be injected into openings 71 formed by the aligned holes 64 and voids 52 using, for instance, a pressurized cement gun or other known injection instrument. The intrusion of the bonding material can replace normal cancellous bone and results in the creation of non-biologic regions. These non-biologic regions are incapable of biologic bone remodeling, such bone remodeling representing an appropriate response to redistribution of forces in the new construct.

Once the bonding material is delivered, the patellar resurfacing implant 72 can be implanted, for example, by inserting the projections 78 into the openings 71 formed by the aligned voids 52 and holes 64. In other words, the projections 78 can extend through the holes 64 of the load-sharing implant 62 and into the voids 52 of the resected patella bone 50. The engaging surface 76 can contact the resected patella surface 56 and the superior surface 68 of the load-sharing implant 62.

The patellar resurfacing system as disclosed herein can incorporate into the native residual bone. Once incorporated, the system (including the load-sharing implant 62) can serve as a load sharing device with the aforementioned forces F, C dampened by the load-sharing implant 62. With this load-sharing implant 62 accepting a portion of the forces F, C (shown in FIG. 5) on the patella, the residual bone can be subjected to lower stresses.

Other examples will be apparent to those skilled in the art from consideration of the specification and practice of the examples disclosed herein. It is intended that the specification and examples be considered as exemplary only, with a true scope and spirit of the example being indicated by the following claims.

Additional Notes

The above detailed description includes references to the accompanying drawings, which form a part of the detailed description. The drawings show, by way of illustration, specific examples in which the invention can be practiced. These examples are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A patellar resurfacing system, comprising:
a load-sharing implant having a superior surface, an inferior surface, and at least one hole extending from the superior surface to the inferior surface, the load-sharing implant configured to be received within a corresponding recess formed in a resected patella bone, wherein the load sharing implant is formed of a metallic material, and wherein the superior surface and the inferior surface are parallel to each other; and
a patellar resurfacing implant having an engaging surface for placement against the resected patella bone and the superior surface of the load-sharing implant, the patellar resurfacing implant including at least one projection extending from the engaging surface, wherein the at least one projection is configured to extend through the load-sharing implant hole and into a corresponding void formed in the recess, wherein the patellar resurfacing implant is formed of a polymer.

2. The patellar resurfacing system of claim 1, wherein a diameter of the patellar resurfacing implant is greater than a diameter of the load-sharing implant.

3. The patellar resurfacing system of claim 1, wherein the load-sharing implant is coated with a biologically active coating for stimulating bone healing in the resected patella bone.

4. The patellar resurfacing system of claim 1, wherein the metallic material includes Nitinol.

5. The patellar resurfacing system of claim 1, wherein the load-sharing implant includes a plurality of holes and the patellar resurfacing implant includes a plurality of projections.

6. The patellar resurfacing system of claim 5, wherein a number of holes in the load-sharing implant is at least one of:
  equal to or greater than a number of projections of the patellar resurfacing implant.

7. The patellar resurfacing system of claim 5, wherein each projection of the plurality of projections is configured to be received within a corresponding hole of the load-sharing implant.

8. The patellar resurfacing system of claim 5, wherein each hole of the plurality of holes is equidistant from the other holes.

9. The patellar resurfacing system of claim 1, wherein the hole is a first hole and the load-sharing implant includes a second hole and a third hole, and wherein the projection is a first projection and the patellar resurfacing implant includes a second projection and a third projection.

10. A method of resurfacing a patella bone, comprising:
  resecting a patella bone to form a resected patella bone having a resected patella surface;
  forming a recess in the resected patella bone, the recess having a recessed patella surface;
  forming at least two voids in the recessed patella surface;
  implanting a load-sharing implant into the recess, the load-sharing implant having a superior surface, an inferior surface, and at least two holes extending from the superior surface to the inferior surface, wherein a first hole is aligned with a first void and a second hole is aligned with a second void, and wherein, when the load-sharing implant is implanted into the recess, the superior surface of the load-sharing implant is substantially flush with the resected patella surface; and
  implanting a patellar resurfacing implant into the resected patella bone, the patellar resurfacing implant including an engaging surface and at least two projections extending from the engaging surface.

11. The method of claim 10, wherein implanting the patellar resurfacing implant in the resected patella bone includes inserting a first projection through the first hole of the load-sharing implant and into the first void formed in the recessed patella surface and inserting a second projection through the second hole of the load-sharing implant and into the second void formed in the recessed patella surface.

12. The method of claim 11, further including placing the engaging surface of the patellar resurfacing implant against the resected patella surface.

13. The method of claim 11, further including, prior to placing the first second projection in the first and second void, injecting a bonding material into at least one of:
  the first void formed in the recessed patella surface, the second void formed in the recessed patella surface, the first hole in the load-sharing implant, and the second hole in the load-sharing implant.

14. The method of claim 13, wherein the bonding material includes a methacrylate.

15. The method of claim 10, wherein implanting the patellar resurfacing implant in the resected patella bone brings the engaging surface into contact with the superior surface of the load-sharing implant.

16. The method of claim 10, wherein inserting the load-sharing implant into the recess includes press fitting the load-sharing implant into the recess.

17. The method of claim 10, wherein the implant includes a metallic material.

18. The method of claim 10, wherein the load-sharing implant includes more than two holes and the patellar resurfacing implant includes a number of projections that is equal to or less than a number of holes in the load-sharing implant.

19. A patellar resurfacing system, comprising:
  a metallic implant having a superior surface, an inferior surface, an edge connecting the superior surface to the inferior surface, and three holes extending through the superior surface to the inferior surface, the metallic implant configured to be received within a corresponding recess formed in a resected patella bone; and
  a patellar resurfacing implant having an engaging surface for placement against the resected patella bone and the superior surface of the load-sharing implant, the patellar resurfacing implant including three projections extending from the engaging surface, wherein each projection is configured to extend through a corresponding hole and into a corresponding void formed in the recess.

* * * * *